(12) United States Patent
Vrdoljak et al.

(10) Patent No.: US 8,881,335 B2
(45) Date of Patent: Nov. 11, 2014

(54) STEAM APPLICATORS

(75) Inventors: Ognjen Vrdoljak, Laval (CA); Mark Rosenzweig, Chestnut Hill, MA (US); Maximilian Rosenzweig, Montreal (CA); Aviva Rosenzweig, legal representative, Montreal (CA)

(73) Assignee: Euro-Pro Operating LLC, Newton, MA (US)

( * ) Notice: Subject to any disclaimer, the term of this patent is extended or adjusted under 35 U.S.C. 154(b) by 84 days.

(21) Appl. No.: 12/779,507

(22) Filed: May 13, 2010

(65) Prior Publication Data

US 2010/0269287 A1  Oct. 28, 2010

Related U.S. Application Data

(63) Continuation of application No. 12/567,726, filed on Sep. 25, 2009, now abandoned, which is a continuation-in-part of application No. 12/554,477, filed on Sep. 4, 2009, now abandoned.

(60) Provisional application No. 61/155,350, filed on Feb. 25, 2009.

(51) Int. Cl.
*A47L 13/16* (2006.01)
*A47L 9/02* (2006.01)
*A61L 2/07* (2006.01)

(52) U.S. Cl.
CPC .......................................... *A61L 2/07* (2013.01)
USPC ............................................. 15/209.1; 15/320

(58) Field of Classification Search
USPC ................. 15/320–322, 49.1, 97.1, 393, 403, 15/209.1
See application file for complete search history.

(56) References Cited

U.S. PATENT DOCUMENTS

| | | | |
|---|---|---|---|
| 1,195,190 A | 8/1916 | Dunlap | |
| 3,546,428 A * | 12/1970 | Omohundro | 392/404 |
| D425,678 S | 5/2000 | Hull et al. | |
| D496,138 S | 9/2004 | Treacy | |
| 6,813,801 B2 | 11/2004 | Tanaka et al. | |
| D500,183 S | 12/2004 | Bensussan et al. | |
| 7,269,878 B2 | 9/2007 | Reese | |
| 7,310,850 B2 | 12/2007 | Ge | |
| 7,392,564 B1 | 7/2008 | Ferris | |
| 7,475,448 B2 | 1/2009 | Rosenzweig et al. | |
| 7,600,401 B2 | 10/2009 | Rosenzweig | |
| D604,468 S | 11/2009 | Hirata et al. | |
| D608,965 S | 1/2010 | Tanaka et al. | |

(Continued)

FOREIGN PATENT DOCUMENTS

| | | |
|---|---|---|
| CN | 2525928 Y | 12/2002 |
| CN | 2576359 | 10/2003 |

(Continued)

OTHER PUBLICATIONS

Evaluation Report for Chinese Application No. 201020138431.1.

(Continued)

*Primary Examiner* — Robert Scruggs
(74) *Attorney, Agent, or Firm* — Wolf, Greenfield & Sacks, P.C.

(57) ABSTRACT

Steam applicators, steam applicator frames, and steam appliance systems in which a steam applicator can be maneuvered to clean and sanitize all kinds of surfaces, not merely floors.

25 Claims, 18 Drawing Sheets

(56) References Cited

U.S. PATENT DOCUMENTS

| | | |
|---|---|---|
| 7,669,280 B2 | 3/2010 | Rosenzweig |
| 7,930,794 B2 | 4/2011 | Tsutanaga et al. |
| 2002/0108209 A1 | 8/2002 | Peterson |
| 2005/0066471 A1 | 3/2005 | Miller et al. |
| 2006/0000049 A1* | 1/2006 | Rosenzweig ................ 15/322 |
| 2006/0000241 A1 | 1/2006 | Rosenzweig |
| 2006/0010633 A1 | 1/2006 | Tanaka |
| 2007/0020020 A1 | 1/2007 | Bobrosky et al. |
| 2007/0130719 A1* | 6/2007 | Zhou ................ 15/320 |
| 2008/0066789 A1 | 3/2008 | Rosenzweig et al. |
| 2008/0216269 A1 | 9/2008 | Tsutanaga et al. |
| 2009/0223540 A1 | 9/2009 | Rosenzweig et al. |
| 2009/0307860 A1 | 12/2009 | Tsuchiya et al. |
| 2010/0212098 A1 | 8/2010 | Vrdoljak |

FOREIGN PATENT DOCUMENTS

| | | |
|---|---|---|
| CN | 1794942 A | 6/2006 |
| CN | 2894596 Y | 5/2007 |
| CN | 2907932 Y | 6/2007 |
| CN | 101019749 | 8/2007 |
| CN | 101116603 | 2/2008 |
| CN | 201019688 Y | 2/2008 |
| CN | 201127588 Y | 10/2008 |
| CN | 201676837 U | 12/2010 |
| DE | 2527207 A1 | 12/1976 |
| EP | 0827709 A2 | 3/1998 |
| JP | 09-238872 A | 9/1997 |
| JP | 11-104051 A | 4/1999 |
| JP | 2002-102130 A | 4/2002 |
| KR | 20-0405606 Y1 | 1/2006 |
| WO | WO 2008/016761 A2 | 2/2008 |
| WO | WO 2008/096950 A1 | 8/2008 |
| WO | WO 2009/111770 A1 | 9/2009 |

OTHER PUBLICATIONS

Report of Utility Model Technical Opionion for JP 2010-001170 mailed Jun. 15, 2011.

International Search Report and Written Opinion dated Jun. 18, 2010 for International Application No. PCT/US2010/000555.

Novelty Evaluation Report for Chinese Application No. 20100138431.1.

Chinese Search Report mailed Dec. 31, 2012 for corresponding Chinese Application No. 201010135193.3.

* cited by examiner

STEAM APPLICATORS

RELATED APPLICATIONS

This application is a continuation of U.S. application Ser. No. 12/567,726 filed Sep. 25, 2009 and entitled "Steam Applicators", which is hereby incorporated by reference in its entirety, and which is a continuation-in-part of U.S. application Ser. No. 12/554,477 filed Sep. 4, 2009 and entitled "Flexible Steam Frame for Steam Appliance," which is hereby incorporated by reference in its entirety and which claims the benefit of U.S. Provisional Patent Application Ser. No. 61/155,530, filed Feb. 25, 2009 and entitled "Flexible Steam Frame for Steam Appliance".

FIELD OF THE INVENTION

The invention relates generally to steam appliances, and more specifically to steam applicators and steam applicator support frames.

DISCUSSION OF THE RELATED ART

Steam appliances are used in the home to apply steam to floors for cleaning and sanitizing. Various types of steam appliances are known, including canister steam appliances and self-contained steam mops, for example. Canister steam appliances typically include a rollable steam generation unit, a hose to transfer the steam from the steam generation unit, a pole, and a mop head or other accessory which is connected to the end of the pole. Self-contained steam mops include a steam generation unit mounted directly on the pole. Handheld steam appliances typically include a container and a nozzle for discharging steam directly from the mouth of the container.

SUMMARY

Embodiments of the invention provided herein are directed to steam applicators, steam applicator frames, and steam appliance systems in which a steam applicator can be maneuvered to clean and sanitize surfaces other than floors.

According to one embodiment of the invention, a steam applicator frame for supporting a steam-permeable material comprises a base, a plurality of support elements extending from the base and arranged such that the base and the support elements define a chamber, and a steam inlet opening to introduce steam into the chamber. The chamber is open at a distal end.

According to another embodiment of the invention, a steam applicator frame for supporting a steam-permeable material includes a base, a plurality of support elements extending from the base and arranged such that the base and the support elements form a chamber, and a steam inlet opening to introduce steam into the steam applicator frame. Exterior surfaces of the support elements are substantially planar and one or more groups of the support elements are each arranged to be substantially co-planar with each other.

According to a further embodiment of the invention, a steam applicator frame for supporting a steam-permeable material includes a base, a handle extending from the base, and a plurality of support elements extending from the base and arranged such that a steam-permeable material can be placed over the support elements to form steam-permeable surfaces. A steam inlet opening to introduce steam into the steam applicator frame is included. The steam applicator frame also includes a steam-impermeable barrier positioned between the handle and the support elements.

According to another embodiment of the invention, a steam applicator includes a steam-permeable material in the shape of a bag, and a frame supporting the steam-permeable material. The frame includes a base, a plurality of support elements extending from the base, the steam-permeable material being positioned over the support elements, and a steam inlet opening to introduce steam into an interior volume of the frame. The support elements are arranged such that when steam is introduced into the interior volume, the steam can flow through at least a first surface of the steam-permeable material and a second surface of the steam-permeable material. Each of the first and second surfaces extends directly from the base, and the first surface converges with the second surface to form an angle.

The present disclosure also provides for a flexible steam frame for a steam appliance including a base member having a steam inlet and a steam outlet; and a plurality of flexible elements extending from the base at the steam outlet to form an internal space for distribution of steam. In one embodiment, the elongated elements are thin metallic or plastic members about 5 to about 8 inches long connected to the outlet end of the base. They generally are stainless steel and may be individual mounted elements or formed from a common base and fan out in an arc between about 20 to about 90 degrees. Bands are flat with are inwardly bent end sections about one-half to about one inch long with the ends overlapping. Wires extend out from the base and may be bent 90 degrees at the end and return to the base. A steam towel substantially matching the shape of the frame formed by the elements is fitted over the frame. There may be an opening on one or two sides to allow the towel to be placed over the bands and secured by Velcro strips attached to the open edge or edges. The towel can be secured by a plastic zipper. The steam hose may be permanently or removably attached to the inlet end of the base.

Various embodiments of the present invention provide certain advantages. Not all embodiments of the invention share the same advantages and those that do may not share them under all circumstances.

Further features and advantages of the present invention, as well as the structure of various embodiments of the present invention are described in detail below with reference to the accompanying drawings.

BRIEF DESCRIPTION OF THE DRAWINGS

The accompanying drawings are not intended to be drawn to scale. For purposes of clarity, not every component may be labeled in every drawing. In the drawings.

DETAILED DESCRIPTION

Figure 1:
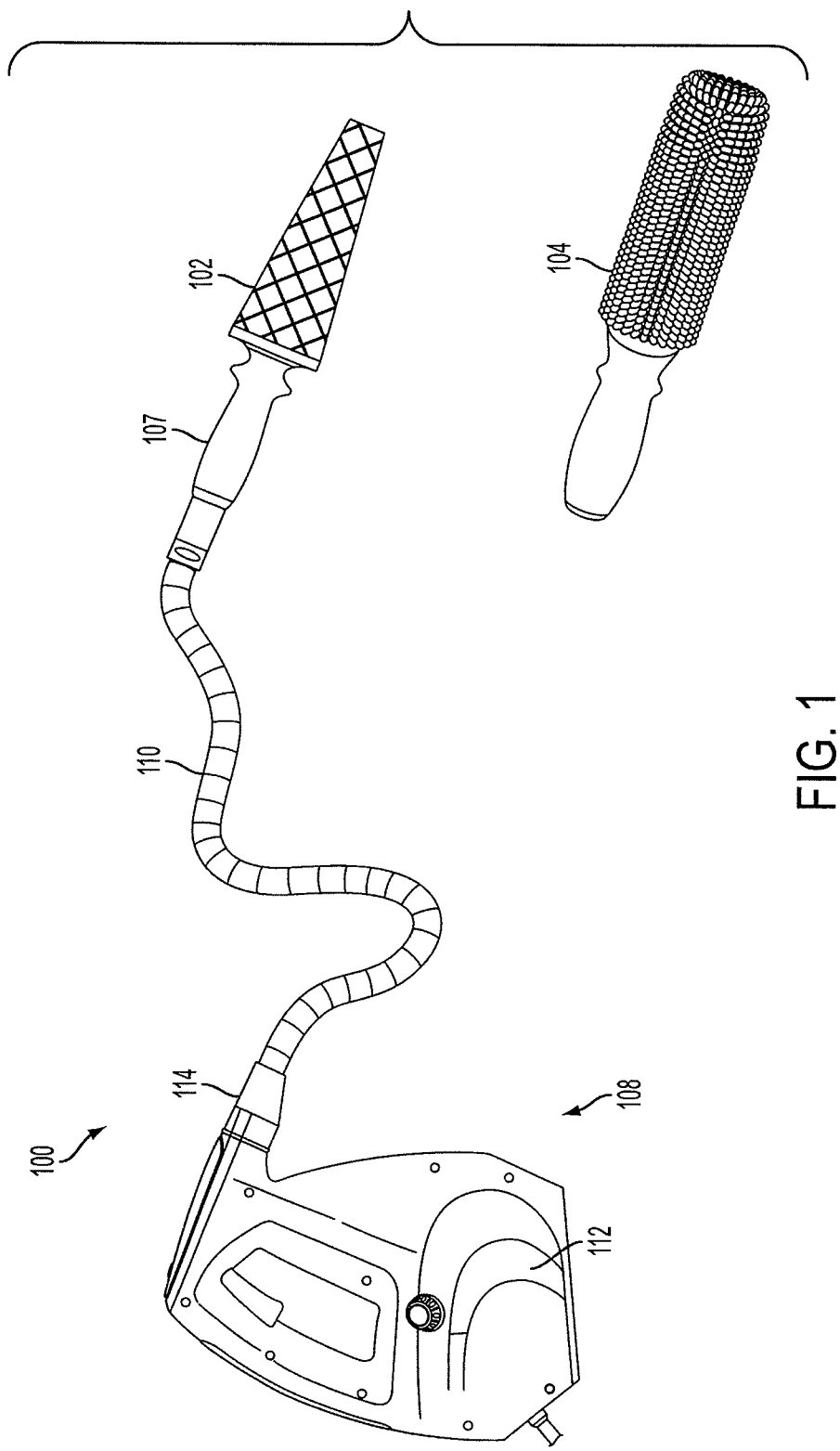
FIG. 1 is a side view of a steam appliance system according to one embodiment of the invention.

Embodiments of the invention provided herein are directed to steam appliance systems in which a steam applicator can be maneuvered to clean and sanitize all kinds of surfaces, not merely floors. For example, the steam appliance system may be used to apply steam to oven hoods, countertops, appliances, walls, ceilings, glass surfaces, bathroom fixtures, upholstery, garments, etc. The steam appliance may include a portable steam generation unit and a steam conduit which guides steam to the steam applicator. In some embodiments, the portable steam generation unit is handheld, while in other embodiments the steam generation unit may include a shoulder strap, or include wheels or other rollers. Several different steam applicators may be provided with the system so that a steam applicator which is well-suited to a particular task may be used.

In some embodiments, a steam applicator may be provided which includes a removable steam-permeable material and a support frame for shaping and/or supporting the steam-permeable material. The steam-permeable material may be a fabric in the shape of a bag (or other flexible container) which can be placed over support elements of the support frame to form a substantially enclosed volume. Such an embodiment may be referred to as a steam pocket. Steam is introduced into the enclosed volume of the steam pocket, and the steam emanates from surfaces of the steam pocket to clean and sanitize objects and household surfaces.

One or more of the steam applicators may have particular characteristics which are helpful for cleaning corners, edges, uneven surfaces, inside small spaces, and/or within partially enclosed areas. For example, in some embodiments, a steam applicator has a shape and/or flexibility which is well-suited for insertion into tight spaces, yet also includes large surface areas for cleaning larger areas such as walls, floors or countertops.

For example, a wedge-shaped steam pocket may be placed over a suitably-shaped support frame to form a steam applicator with a thin leading edge which can be inserted under furniture or into crevices. The leading edge of the steam applicator may have a flexibility which permits increased reach into tight or oddly-shaped gaps. In some embodiments, the frame support elements do not extend to the leading edge of the steam pocket, which provides further flexibility. The same wedge-shaped steam pocket also may include large flat surfaces on the top, bottom and/or sides for cleaning countertops, oven hoods, walls, etc.

The steam applicator releases steam from multiple surfaces in some embodiments. For example, the wedge-shaped steam pocket may provide steam from a top surface, a bottom surface, and/or side surfaces, thereby allowing the steam applicator to be moved along an edge, such as where a wall meets a ceiling, to simultaneously clean two surfaces. A box-shaped steam pocket could also clean two or more surfaces at the same time, and include a front steam application surface. A rear surface may include a steam-impermeable material to reduce steam near a handle for the steam applicator, while in other embodiments, the rear surface may be primarily a steam-permeable surface.

Flat frame support elements are provided in some embodiments, and may be beneficial for providing a progressively increasing flexibility of the frame toward the distal end of the frame. The flat frame support elements also may help a user apply distributed pressure on a surface to be cleaned. In some cases, the flat support elements of a support frame may have a reduced thickness at their leading, free ends, which may reduce the chances of the support element catching on an edge (such as an edge of a countertop) as the steam applicator is inserted into a gap (such as a gap between the countertop edge and a kitchen appliance).

The frame support elements (flat or otherwise) may be configured to form a chamber having an open front end. In this manner, when a steam pocket is mounted to the support frame, a preferential steam pathway may be formed at the front end where no support elements are present to impede steam release. A preferential steam pathway at the front end may provide one or more benefits as described in more detail further below.

In some embodiments, an elongated cylindrical applicator frame and steam pocket may be provided. The cylindrical steam pocket may be helpful for dusting and reaching surfaces within partially enclosed spaces that a steam pocket with a larger cross-section or shorter length might not be able to reach. Steam applicators may have other shapes as well, some examples of which are described further below.

Various materials may be used for a steam pocket. For example, a shag material may be used in some embodiments, while in other embodiments a quilted microfiber fabric may be used. In some embodiments, a steam pocket may have one or more surfaces which include a coarse or abrasive material, and is still other embodiments, a non-streak material may be provided.

A steam appliance system 100 including two attachable steam applicators—a wedge shaped steam applicator 102 and a cylindrically shaped steam applicator 104—is shown in FIG. 1. Steam applicators 102 and 104 each may include a handle 107 which is permanently or detachably attached to the applicator. In the embodiment of FIG. 1, steam appliance system 100 includes a steam generation unit 108, a steam conduit 110, and attached steam applicator 102. Steam generation unit 108 may include any suitable type of steam generation system, for example a cool water reservoir 112 and an aluminum die-cast steam generator (not shown). In some embodiments, water may be heated to its boiling point within its reservoir to create steam. It should be noted that the method of steam generation is not intended to be a limiting aspect of the invention.

In some embodiments, the steam generation unit 108 is handheld, while in other embodiments the steam generation unit may include a shoulder strap, or include wheels or other rollers.

Steam conduit 110 is a flexible hose in some embodiments. Steam conduit 110 may be attachable to steam generation unit 108 with any suitable attachment 114, including a removable connector, such as a bayonet connector.

Figure 2:
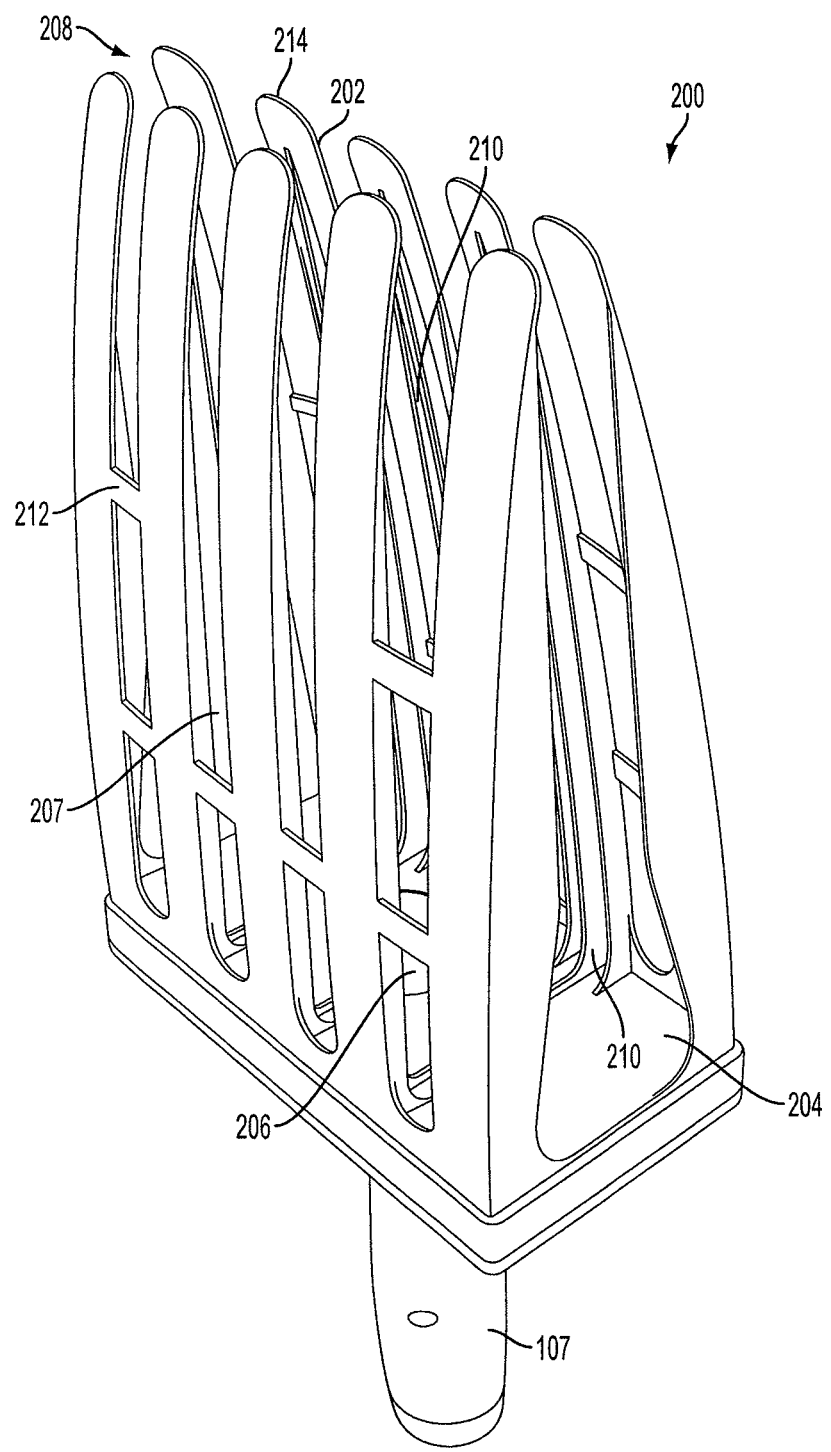
FIG. 2 is a perspective view of a support frame according to one embodiment of the invention.

A support frame 200 having a plurality of support elements 202 attached to a base 204 is shown in FIG. 2. In the embodiment of FIG. 2, support elements 202, in combination with base 204, form a chamber into which steam may be introduced through a steam inlet opening 206. When a steam-permeable material is placed over the support frame, a steam pocket is formed. Steam from within the chamber passes into the material through gaps 207 in the support elements, and the steam emanates from the steam pocket to clean and sanitize surfaces.

Support frame 200 is configured to have an open distal end 208 which may provide one or more benefits. For example, open distal end 208 allows for increased flexibility at the distal end, which can help when attempting to place the steam applicator into tight or oddly-shaped spaces. Additionally, with no support elements at distal end 208, additional surface area is available for steam release. Such a configuration may create a preferential pathway for steam, which may be helpful when cleaning with the distal end of the support frame. When moving the steam applicator forward with handle 107, distal end 208 becomes the leading edge of the steam applicator, and additional steam release at the leading edge may help provide additional moisture ahead of the steam applicator. During use for wrinkle removal, moisture at the leading edge of the steam applicator helps to loosen fibers, while the heat from the trailing portion of the applicator helps to align fibers.

To navigate uneven surfaces, edges and corners, a flexible support frame is provided in some embodiments. The flexibility may increase toward distal end 208 to allow the thinner portions of the steam pocket to be more compliant with the surfaces being cleaned. Support ribs 210 may be provided on one or more of support elements 202, and support ribs 210 may taper as they move toward distal end 208. Cross-braces 212 may be provided at various location on support frame 200, and the number and/or thickness of cross-braces 212 may decrease toward distal end 208.

Support elements 202 are flat, which may help a user apply distributed pressure on a surface to be cleaned. Additionally, distal-facing leading edges 214 of support elements 202 may reduce the chances of the support element catching on an edge or an object as the steam applicator is passed through crevices or into gaps.

Steam may be introduced into the chamber of the steam applicator through steam inlet opening 206. In some embodiments, a steam conduit may enter the chamber through steam inlet opening 206 and inject steam directly into the chamber. In other embodiments, a steam conduit may end prior to reaching the chamber portion of the steam applicator, and steam may travel into the chamber via steam inlet opening 206.

Figure 3:
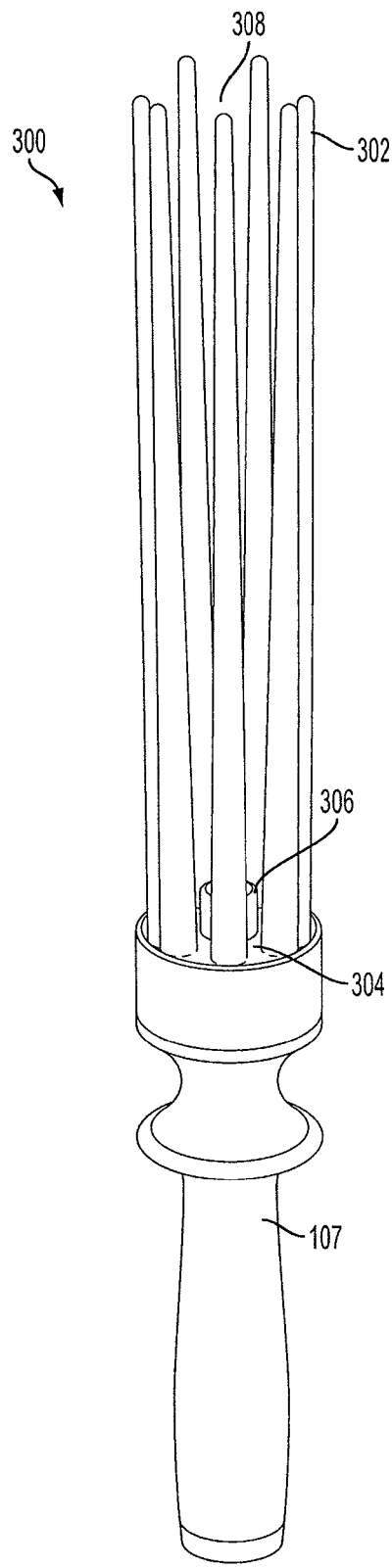
FIG. 3 is a perspective view of a support frame according to another embodiment of the invention.

An elongated, cylindrically-shaped support frame 300 is shown in FIG. 3. As with the embodiment shown in FIG. 2, a chamber formed by a base 304 and support elements 302 includes an open distal end 308. To provide progressively increasing flexibility in the distal direction, support elements 302 have a tapering diameter. In some embodiments, the diameter of the support elements may be constant, or may increase toward the distal end. In some embodiments, support elements 302 may bow slightly outwardly in the radial direction.

A steam inlet opening 306 is provided on base 304. In some embodiments, a steam conduit may extend within and along the chamber formed by base 304 and support elements 302 to release steam at one or more locations within the steam pocket.

Handle 107 may permit rotation of support frame 300 relative to an attached steam conduit in some embodiments. The rotation may occur around an end-to-end direction of the steam applicator, and/or about an end-to-end direction of handle 107. In some embodiments, pitch and/or yaw rotations may be permitted as well. A universal joint may be used in addition to, or instead of, the structures described herein.

The steam-permeable materials used with embodiments described herein may be formed of any suitable material. In some embodiments, the steam pocket material is formed with cotton, while in other embodiments, the steam pocket material may be formed with a synthetic fabric such as polyester or polyolefin fiber. A microfiber, such as a polyester microfiber may be used in some embodiments. A shaggy material, such as the material shown on steam applicator 104 may be used, and may be particularly useful for dusting applications.

Figure 4:
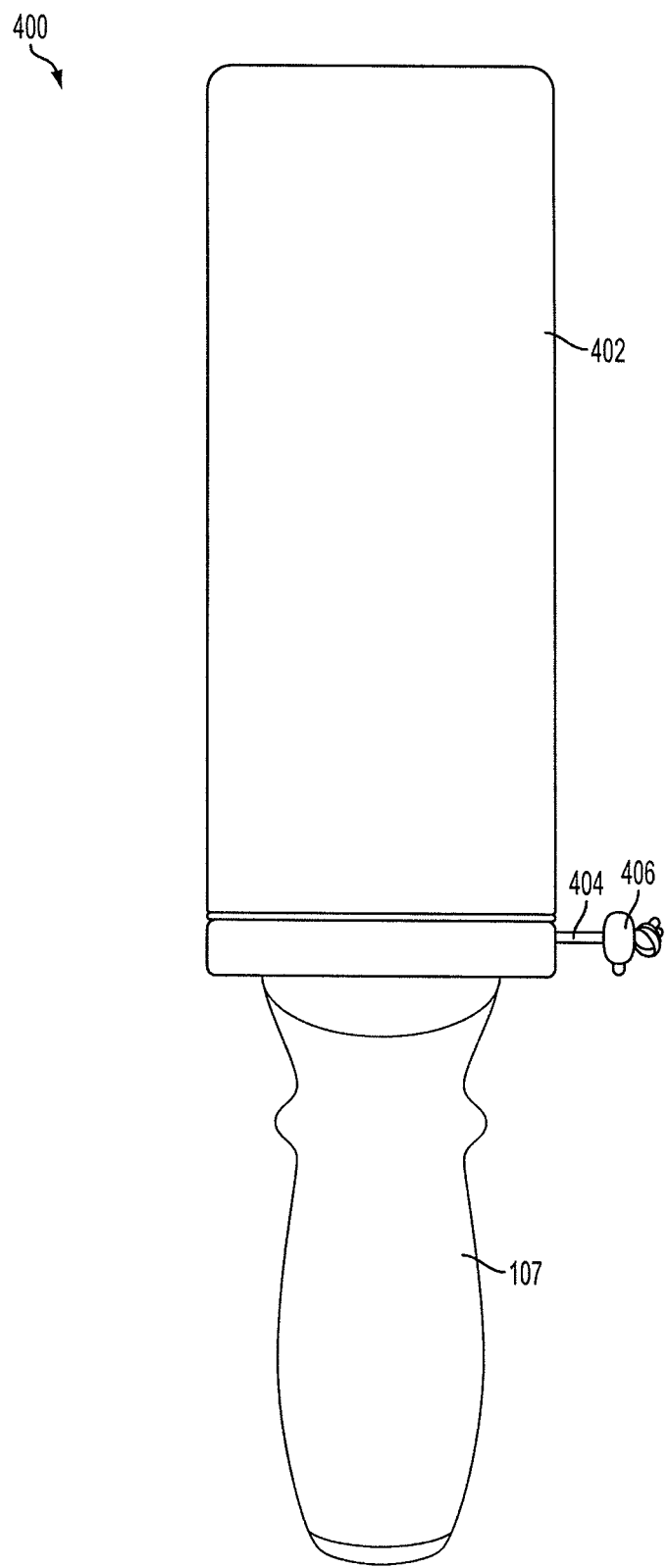
FIG. 4 is a side view of a steam applicator according to a further embodiment of the invention.

FIG. 4 shows a steam applicator 400 including a steam pocket 402 formed with a steam-permeable material. Steam pocket 402 includes an cinch cord 404 and a cord lock 406. Cord 404 may encircle handle 107 or a base of the support frame and be locked with cord lock 406 to prevent steam from being released from steam pocket 402 near a user's hand. In some embodiments, a base of the support frame may include steam-permeable material.

In some embodiments, frames and steam applicators described herein may be used in conjunction with a long handle to increase the reach of the system.

Components described herein may be included as part of a kit and include instructions for assembly and operation.

The present disclosure provides for improved steam appliances. More particularly, the present disclosure provides for a flexible steam frame for a steam appliance for use in cleaning various surfaces (e.g., uneven surfaces and corner regions).

Figure 5:
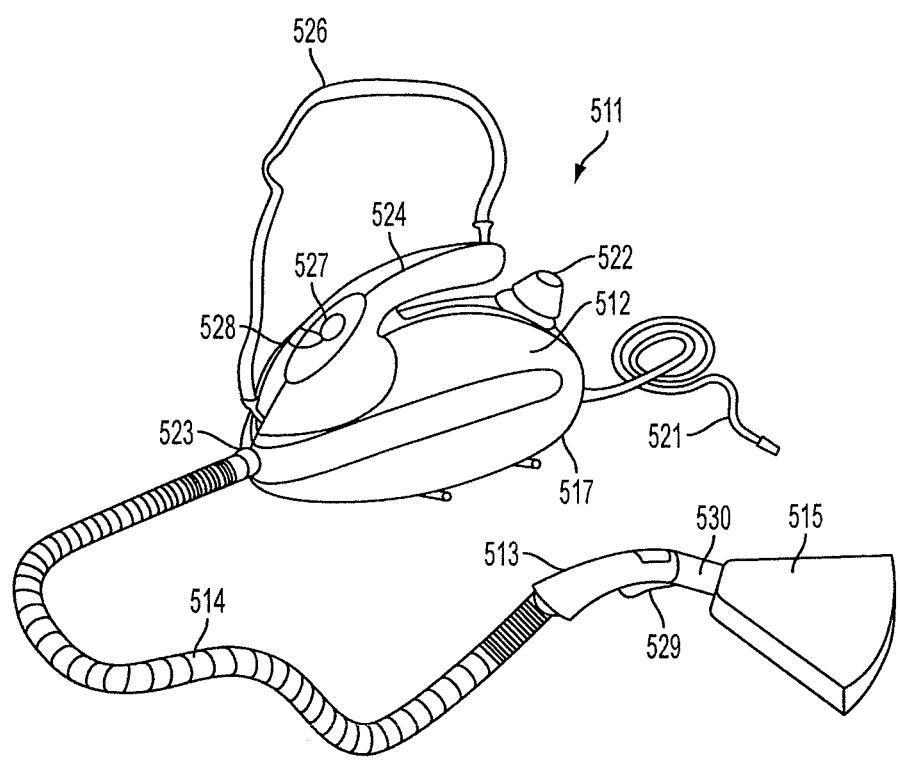
FIG. 5 is a perspective view of a steam appliance including the flexible steam frame constructed and arranged in accordance with the present disclosure.

Referring to the drawings, and in particular to FIG. 5, there is illustrated a perspective view of a steam appliance or steam cleaning device 511 including a main body or housing 512. A steam release hand grip 513 is coupled to housing 512 by a flexible hose 514 having a flexible steam frame 515 constructed and arranged in accordance with the present disclosure installed. In exemplary embodiments, steam frame 515 mounted on the distal nozzle end of hand grip 13 includes a steam towel or the like at the distal end.

Housing 512 of steam cleaning device 511 includes a water inlet 522 and an internal water reservoir 517 with heating elements connected to a power source by a power cord 521. Steam generated in reservoir 517 exits by steam outlet 523 with flexible hose 514 coupled thereto. Main body 512 may be outfitted with a handle 24 and a strap 26 for conveniently lifting and carrying main body 512. Main body 512 also includes an on/off switch 527 and an indicator light 528 to indicate when steam temperature is appropriate for use.

Once water has been heated sufficiently to generate steam within main body 512, a user may selectively release steam into flexible steam frame and towel 515 by operation of hand grip 513. In one embodiment, hand grip 513 has an internal cavity and is elongated and curved for conveniently fitting within the hand of a user. Hand grip 513 includes a proximal inlet end with a fitting for securing flexible hose 514 and, its distal outlet end 530 is connected to steam frame 515 in accordance with the present disclosure. Hand grip 513 is fitted with a trigger 529 for selectively releasing and controlling the amount of steam fed into steam frame 515.

Figure 6:
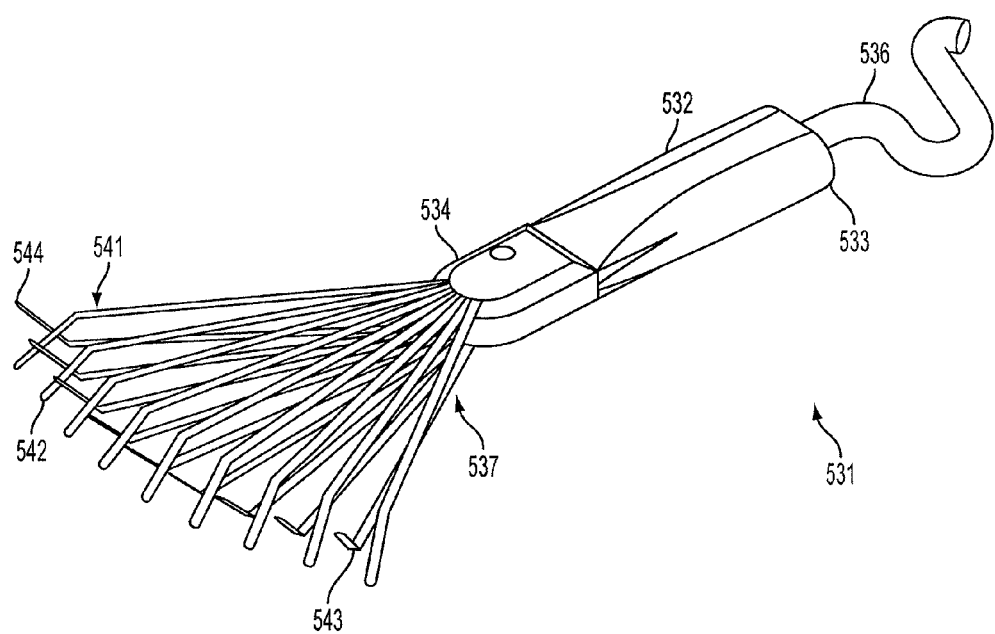
FIG. 6 is a perspective view of a flexible steam frame constructed and arranged in accordance with one embodiment of the present disclosure.

FIG. 6 is a perspective view of a flexible steam frame 531 constructed and arranged in accordance with the present disclosure. Steam frame 531 includes a flat rigid elongated handle 532 substantially equivalent to curved handle 513 having an inlet end 533 and an outlet end 534. Inlet end 533 has a flexible steam hose 536 connected thereto. In an exemplary embodiment, a plurality of flexible bands or fingers 537 arranged in a fan-like shape in two substantially parallel planes are mounted to outlet end 534 of handle 532.

Figure 7:
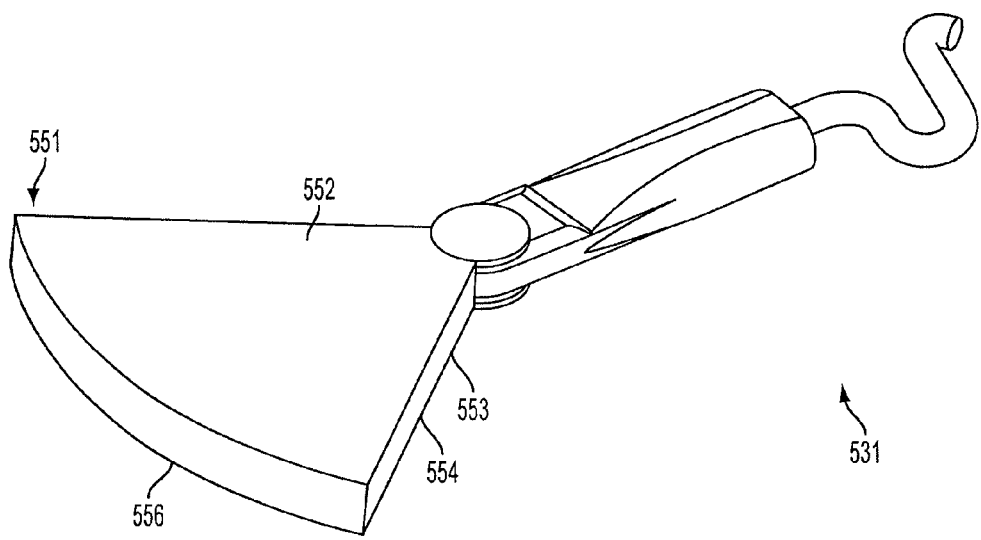
FIG. 7 is a perspective side view of a flexible steam frame with a steam towel attached.
Figure 8:
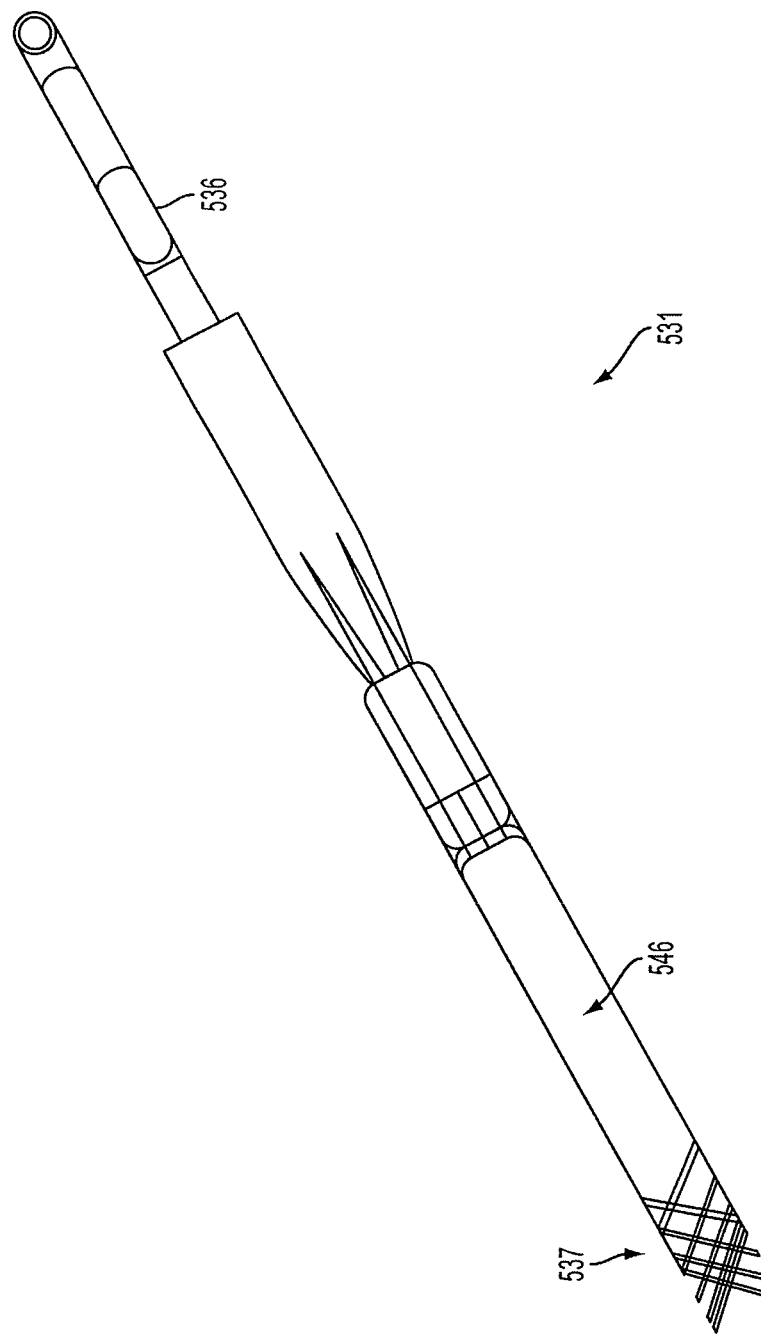
FIG. 8 is a side elevational view of the steam frame of FIG. 6.
Figure 9:
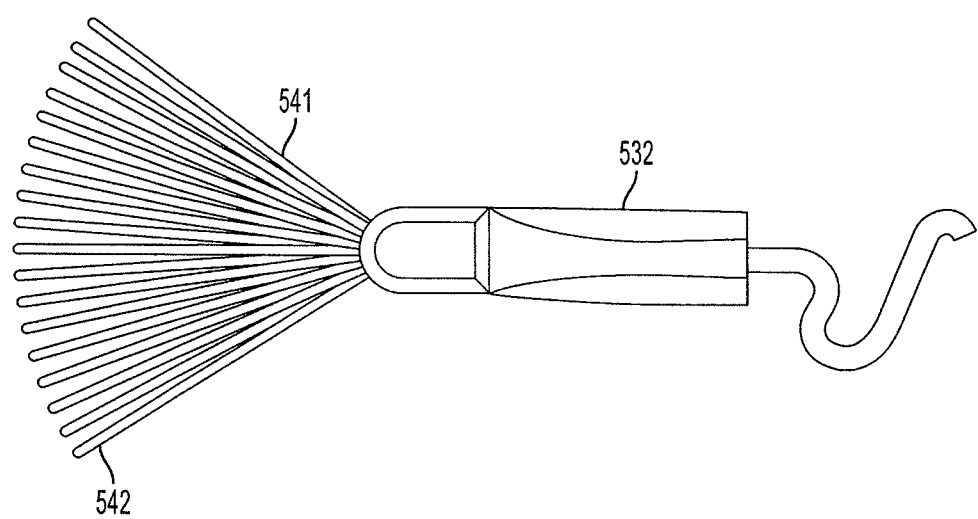
FIG. 9 is a plan view of one side of the flexible steam frame of FIG. 6.

Each band 537 is between about one-eighth to about one-half inches wide, and about 4 to about 7 inches long constructed from a metallic material, such as, for example, stainless steel, or from a plastic material, such as, for example, a polyolefin, polyester or polystyrene. At the distal end, each band 537 includes a bent portion facing the other series of bands. In one embodiment and as depicted in FIG. 6 of a flexible steam frame 531 having an elongated and flattened handle 532, there is an upper fan-shaped set of bands 541, each with a bent portion 542 facing downward. Exemplary flexible steam frame 531 also includes a lower fan-shaped set of bands 543, each with a bent portion 544 facing upward. Bent portions 542 and 544 overlap. Since upper bands 541 and lower bands 543 are spaced apart between about one-quarter to three-quarters of an inch, there is a space 546 created between flexible bands 541 and 543 as shown in the side elevational view of FIG. 8. FIG. 7 shows a steam towel 551 having substantially the same outer shape as flexible band 541 and 543 placed over bands 541 and 543 and secured by Velcro strips or a plastic zipper. Towel 551 includes an upper surface 552 and a matching lower surface 553 and two side edges 554 extending from outlet end 534 of handle 532 and a curved front edge 556.

Towel 551 has at least one split along edge 554 and may have two openings or splits, one on each side at edges 554. The openings are closed with Velcro strips or plastic zippers or the like. Alternately, towel 551 may be split at front edge 556. Bands 541 and 543 and towel 551 are shown in a fan-like shape with an arc at the distal end and front edge 556. This arc may be from about 20° to about 90° to provide suitable steam cleaning areas. Alternately, front edge 556 may be a straight line between the two edges 554.

In an exemplary embodiment, handle 532 is elongated having an oval cross-section and is about 5 inches in length. As shown in FIG. 5, handle 513 may be curved to fit a user's grip comfortably. Hose 514 or 536 may be permanently or removably coupled or attached to inlet end 533 of handle 532. Steam generation may be controlled by on/off switch 527 and applied to steam frame 15 by operation of trigger 529 in handle 513.

Figure 10:
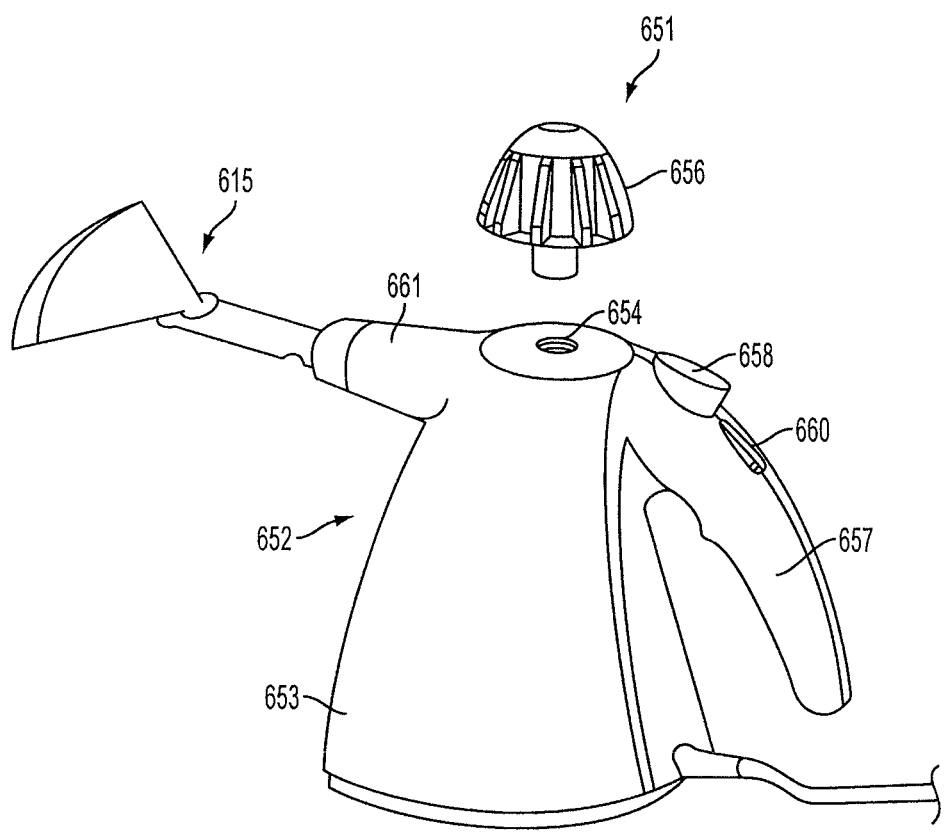
FIG. 10 is a perspective view of a hand-held steam appliance including a flexible steam frame and towel constructed in accordance with the present disclosure.

In an alternative embodiment, FIG. 10 is an elevational view of a hand-held steam appliance or device 651 having a main body 652 with a boiler 653 and an inlet 654 with locking cap 656. A handle 657 is mounted at the top of main body 652 and has a steam release trigger 658 and a trigger release 660 mounted thereon. A nozzle 661 is mounted on main body 652 opposite to handle 657. Steam is transferred from boiler 653 to a location at which discharge of the steam is desired through nozzle 661 and flexible steam frame 615 as shown in FIG. 5. By using compatible couplings for nozzle 661 and frame 615, frame 615 may be directly connected to nozzle 661 or to a hose, such as hose 514 in FIG. 5.

Figure 11:
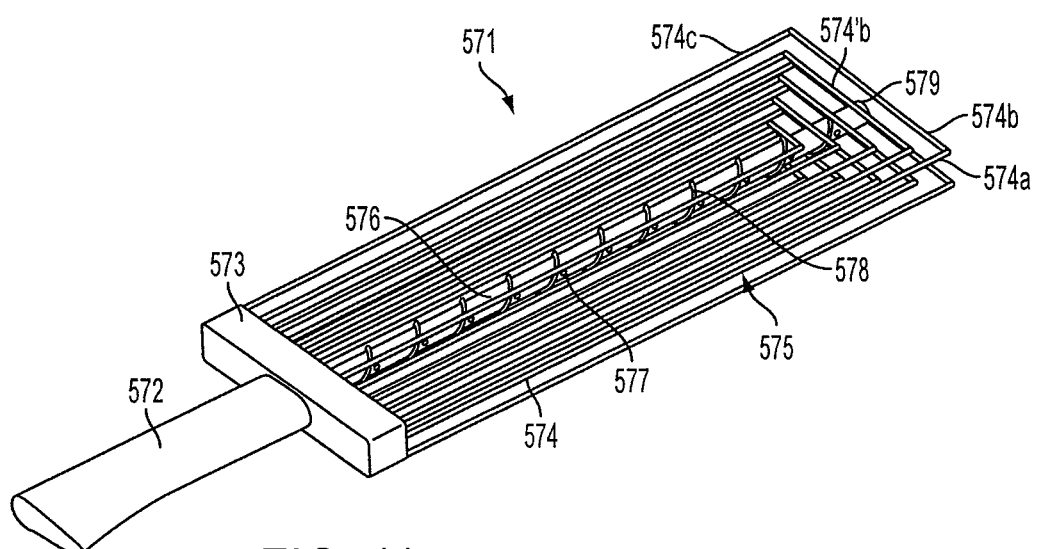
FIG. 11 is a perspective view of a flat wire flexible steam pocket with internal steam distribution prepared in accordance with the present disclosure.

FIG. 11 illustrates a flexible, substantially flat steam frame 571 in accordance with the present disclosure. Frame 571 includes an elongated rigid handle 572 and a perpendicular wire base 573 at the distal end. In exemplary embodiments, handle 572 includes a steam inlet, and base 573 includes a steam outlet. The steam inlet of handle 572 may have a flexible steam hose coupled thereto.

As shown in FIG. 11, a plurality of wires 574 (e.g., elastic metallic wires, plastic wires, etc.) extend from base 573. In an exemplary embodiment, wires 574 are flexible stainless steel wires. Here, wires 574 are arranged in two substantially parallel planes with each wire 574 extending distally from base 573 to form a first leg 574a, a right angle to run substantially parallel to base 573 to form an end section 574b, and which returns to base 573 along second leg 574c. Outer wire 574 is longer than inner wires 574'. Upper and lower wire planes are spaced apart to create a space 575 therebetween (e.g., where steam is introduced). Base 573 typically includes a steam outlet for the introduction and distribution of team to the space 575. In exemplary embodiments, the steam outlet is trumpet-shaped or bell-shaped to ensure even steam distribution (e.g., throughout space 575).

A towel in the form of a steam pocket having two substantially parallel flat surfaces stitched about the two long edges and one short edge to form a pocket may be slipped or positioned over wires 574. The steam pocket is a cloth or towel and may be formed of any suitable fabric such as cotton or a synthetic fabric, such as polyester or polyolefin fiber. Preferably, the fabric is a microfiber. Most preferably, the microfiber is a synthetic polyester microfiber.

Figure 12:
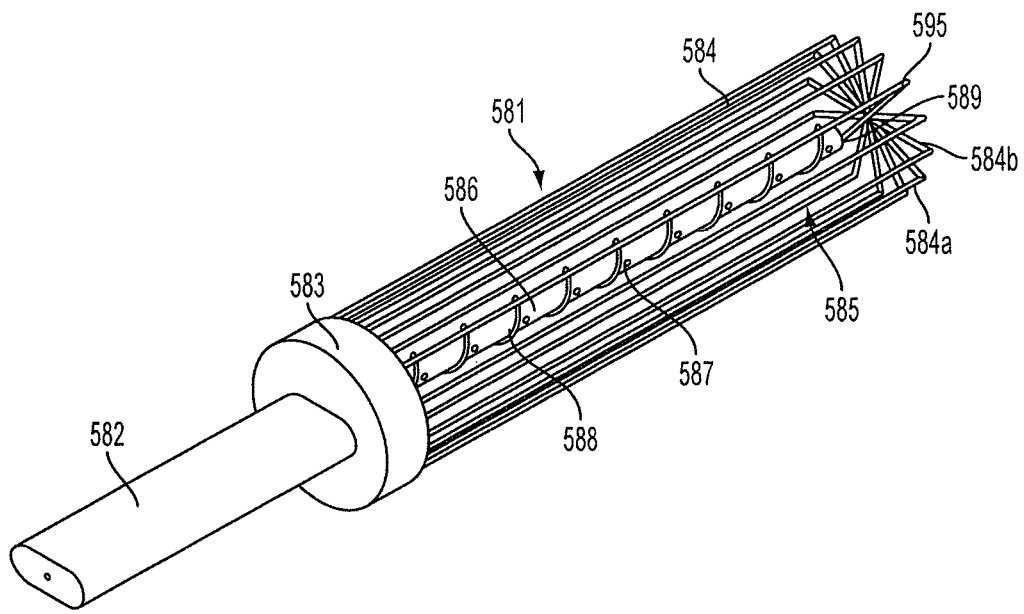
FIG. 12 is a perspective view of a round wire flexible steam pocket with internal steam distribution prepared in accordance with the present disclosure.

FIG. 12 illustrates a flexible wire steam frame 581 in accordance with another embodiment of the present disclosure. As shown in FIG. 12, steam frame 581 is a round, cylindrical or tubular wire steam frame, although the present disclosure is not limited thereto. Frame 581 includes an elongated rigid handle 582 and a circular planar base 583 at the distal end. A plurality of stainless steel wires 584 extend from base 583. Here, wires 584 are arranged along the circumference of base 583 and extend along a first leg 584a and then at substantially right angles to a radial end 584b meeting the other radial ends at an end point 587. This configuration of wires 584 forms an internal cylindrical or tubular space 585 where steam is introduced. In another embodiment, the wires 584 are arranged along the circumference of base 583 and extend distally to a circular end portion (not shown), thereby forming an internal cylindrical or tubular space 585 where steam may be introduced. Alternatively, the wires 584 may form various other shaped or defined internal spaces 585 (e.g., conically shaped internals spaces, frusto-conically shaped internal spaces, tapered internal spaces, rounded and planar internal spaces, etc.) where steam may be introduced.

With reference to FIG. 12, a steam towel in the form of a cylindrical or tubular towel closed at the distal end and secured about base 583 is used. The towel may be secured at base 583 by an elastic or tie band or the like about the distal end of handle 582. As depicted in FIG. 12, the cylindrical or tubular wire steam frame 581 provides an advantageous shape for cleaning various surfaces (e.g., small narrow areas and inside of round-shaped objects). The wires 584 are configured and dimensioned to provide support for the towel so that the towel is kept in contact with the cleaning surface.

In exemplary embodiments and as shown in FIGS. 11 and 12, steam frames 571 and 581 are shown with added internal steam distribution, although the present disclosure is not limited thereto. In both embodiments, handles 572 and 582 are made of plastic (e.g., hard plastic) to provide the base that holds all the parts together and is also user friendly for use. Wires 574 and 584 are fabricated from stainless steel or the like to provide the elasticity and keep the fabric towel stretched and tightened, but wires 574 or 584 may bend when force is applied in order to accommodate different angles of use.

An internal steam distributor is provided to ensure the even steam distribution in internal space 575 and 585 in the form of an internal conduit 576 and 586 that extends from the steam outlet in handle 572 and 582 and base 573 and 583 to wire ends 574b and 584b. In an exemplary embodiment, internal conduit 76 and 86 is made of flexible hose and has openings 577 and 587 on both sides along the length thereof. The end 579, 589 of conduit 576 and 586 is closed to prevent the steam from exiting straight forward.

An elastic spring 578 and 588 made of stainless steel is wrapped around conduit 576 and 586 to provide elasticity for internal conduit hose 576 and 586. Spring 578 and 588 also keeps hose 576 and 586 centered if there is no force applied, but allows bending to accommodate changing the shape of frame 571 and 581 during use.

Figure 13:
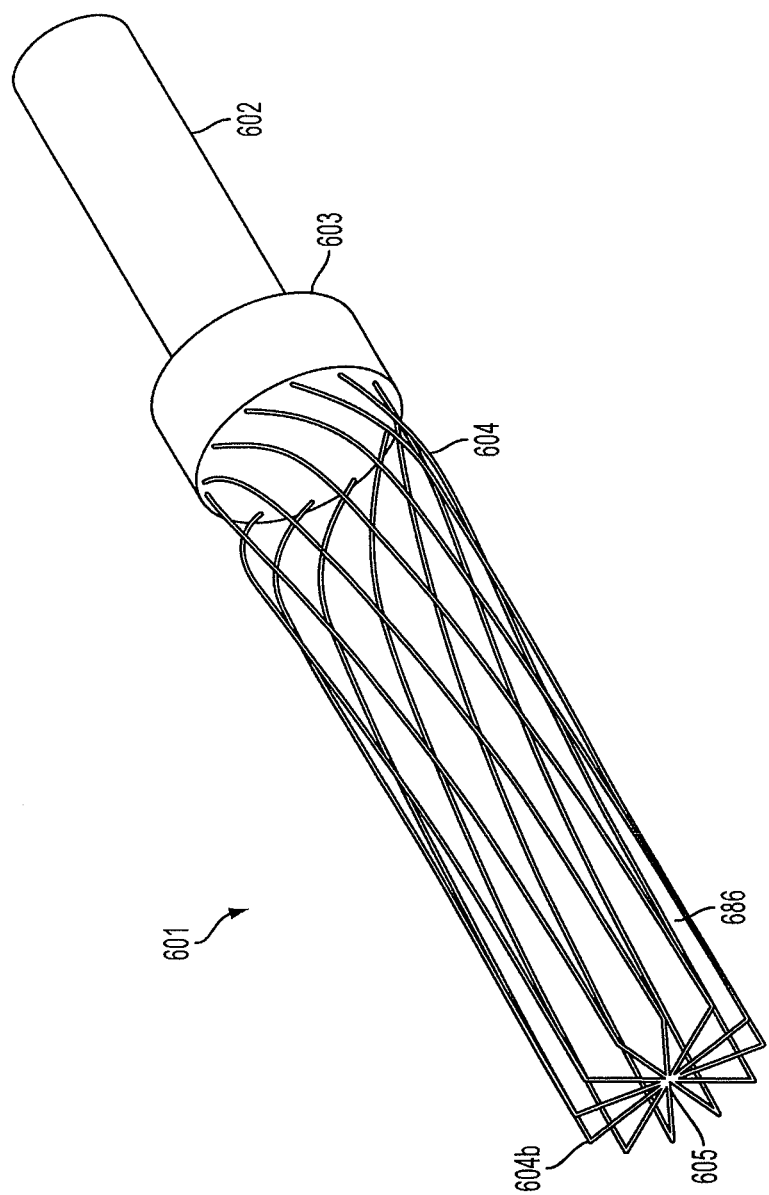
FIG. 13 is a perspective view of an embodiment of a steam frame according to the present disclosure.
Figure 14:
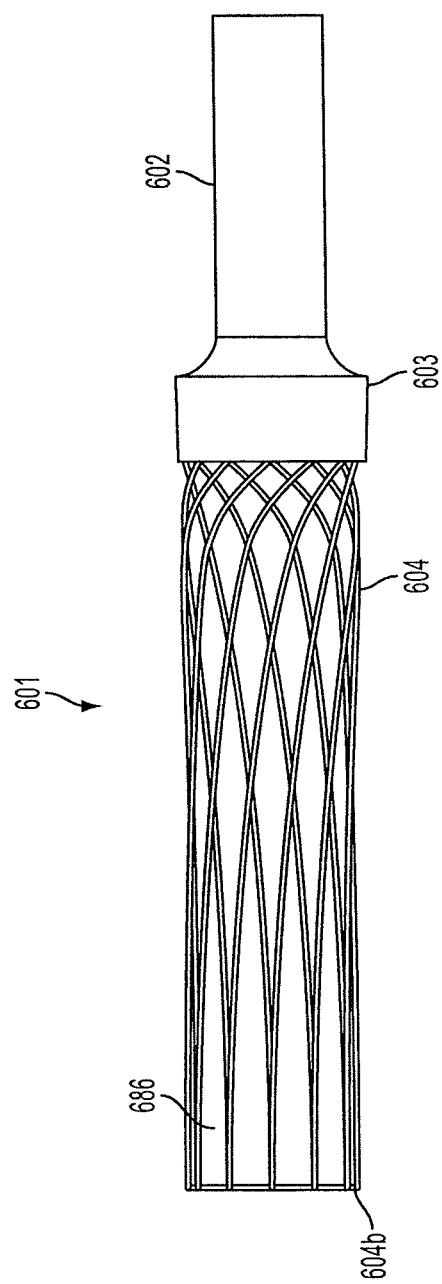
FIG. 14 is a side view of the steam frame of FIG. 13.

In an alternative embodiment and as depicted in FIGS. 13 and 14, steam frame 601 is a flexible, substantially round, cylindrical or tubular wire steam frame having an elongated rigid handle 602 and base 603. A plurality of wires 604 (e.g., stainless steel or plastic wires) extend from base 603. As shown in FIGS. 13 and 14, each wire 584 may be twisted or curved. Wires 604 extend from the base 603 along a curved path defining the cylindrical or tubular shape of the steam frame 601, and then at right angles to a radial end 604b meeting the other radial ends at an end point 605, to thereby define or form the cylindrical or tubular wire shape of steam frame 601. This configuration of wires 604 forms an internal cylindrical or tubular space 686 where steam is introduced. A steam towel in the form of a cylinder or tube closed at the distal end and secured about base 603 may be used. The towel may be secured at base 603 by an elastic or tie band or the like about the distal end of handle 602.

At least one advantage of having twisted or curved wires 604 is that the number of wires in the frame 601 may be kept to a minimum, thereby reducing the rigidity of the frame 601, which reduces the strain on the user's hand during use. In addition, the twisted or curved wires 604 provide increased support for the towel. This configuration also has improved properties for bending or flexibility, and also reduces the strain and/or fatigue of the materials used in the frame 601. As depicted in FIGS. 13 and 14, the cylindrical or tubular shape of steam frame 601 provides, an advantageous shape for cleaning various surfaces (e.g., small narrow areas and inside of round-shaped objects). The wires 604 are configured and dimensioned to provide support for the towel so that the towel is kept in contact with the cleaning surface.

Figure 15:
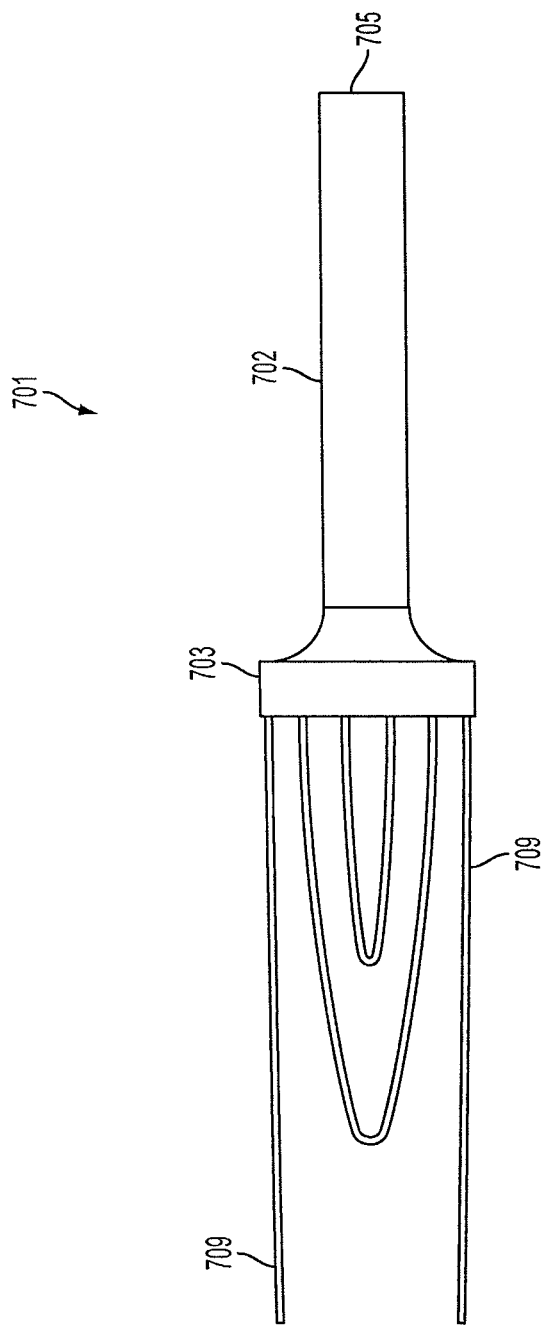
FIG. 15 is a side view of an embodiment of a steam frame according to the present disclosure.
Figure 16:
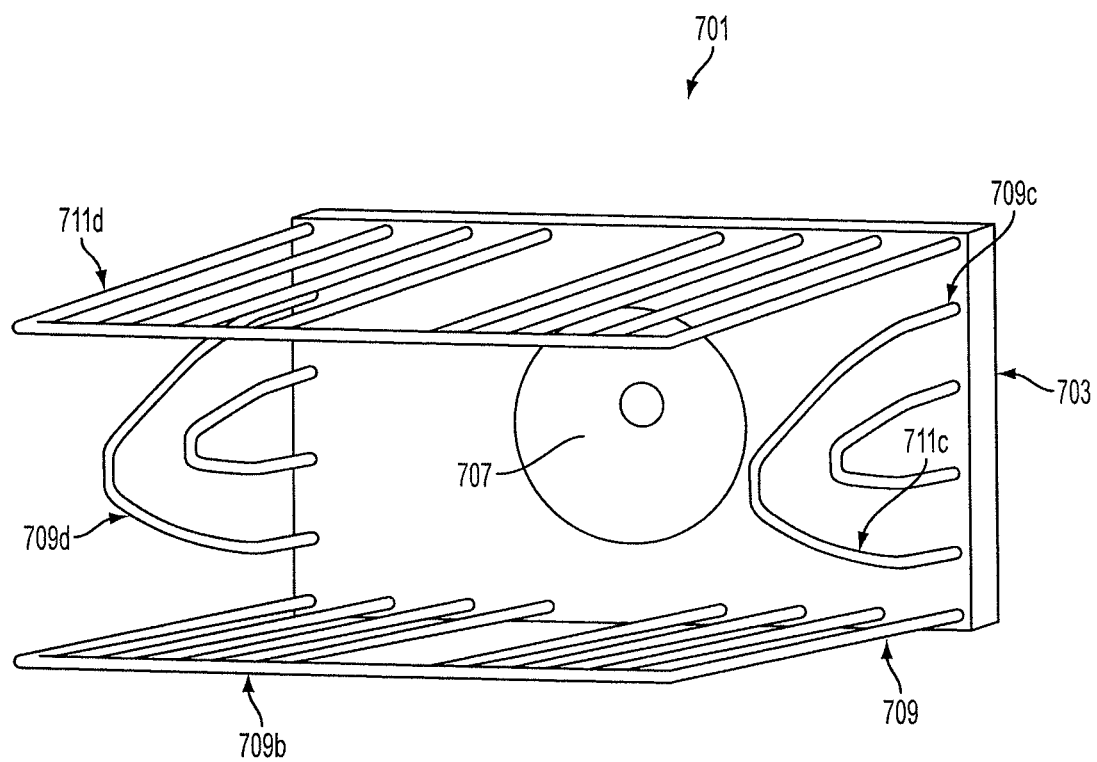
FIG. 16 is a perspective partial view of the steam frame of FIG. 15.

In an alternative embodiment and as depicted in FIGS. 15-16, flexible steam frame 701 includes an elongated rigid handle 702 and a base 703. In exemplary embodiments, handle 702 includes a steam inlet 705, and rigid base 703 includes a steam outlet 707. The steam inlet 705 of handle 702 may have a flexible steam hose coupled thereto. The handle 702 may be fixedly attached (e.g., solidly attached) or coupled to the base 703. Exemplary base 703 takes the form of a rectangular base, although the present disclosure is not limited thereto.

Frame 701 further includes a plurality of wires or bands 709 (e.g., elastic metallic wires, plastic wires, etc.) that extend from base 703. In an exemplary embodiment, wires 709 are flexible stainless steel wires. Frame 701 typically includes at least one upper wire 709a arranged in a first plane and at least one lower wire 709b arranged in a second plane, with the wires 709a, 709b extending distally from base 703. In exemplary embodiments, frame 701 includes at least one upper wire 709a, at least one lower wire 709b, at least one first side wire 709c, and at least one second side wire 709d, all of which extend distally from base 703. In one embodiment, frame 701 includes an upper set of wires 709a, a lower set of wires 709b, and two side sets of wires 709c, 709d, all of which extend distally from base 703. Upper set of wires 709a and lower set of wires 709b may take the form of a substantially planar, rectangularly shaped set of wires, as shown in FIGS. 15 and 16, although the present disclosure is not limited thereto. Rather, upper set of wires 709a and lower set of wires may take a variety of forms (e.g., substantially triangularly or conically shaped, etc.). Moreover, upper set of wires 709a and lower set of wires may take the form of a tapered or flared set of wires. Side sets of wires 709c, 709d typically include curved or tapered portions 711c, 711d. In one embodiment, each set of wires 709 may have different levels of flexibility and/or elasticity.

Figure 17:
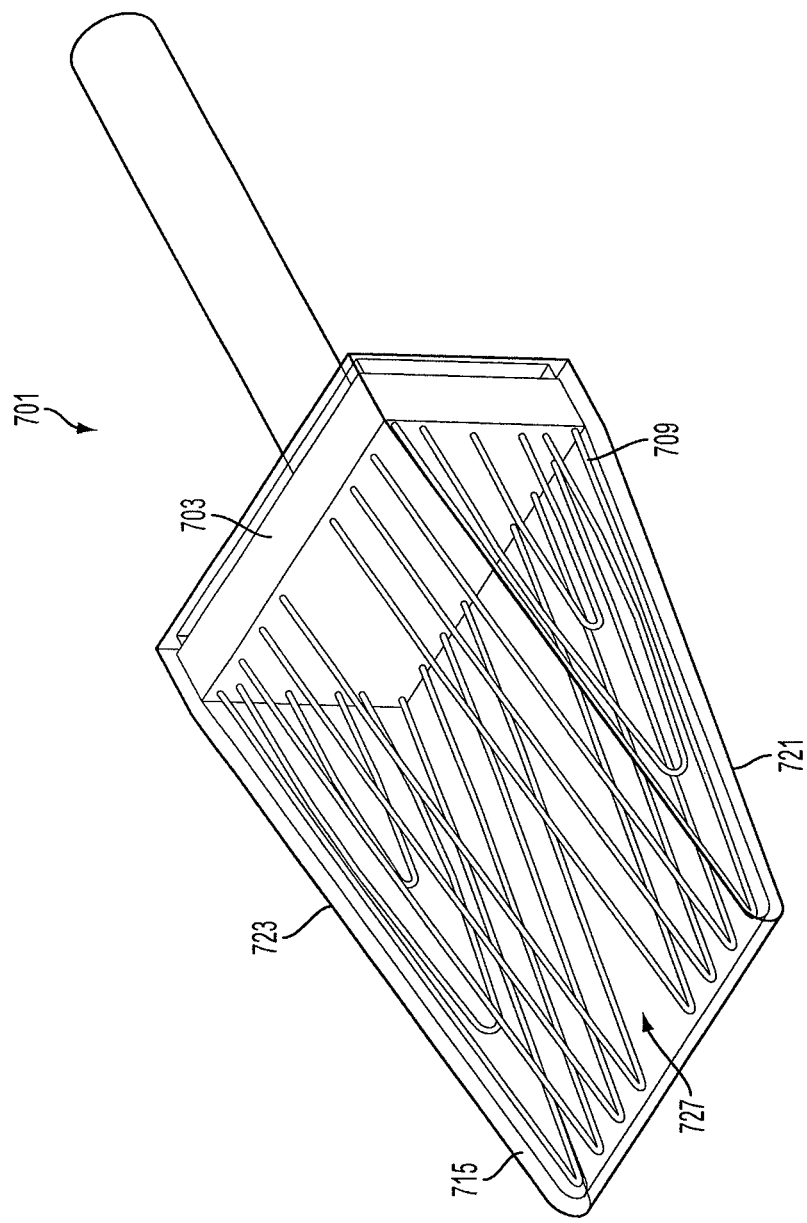
FIG. 17 is a perspective view of the steam frame of FIG. 15, with a steam towel attached.
Figure 18:
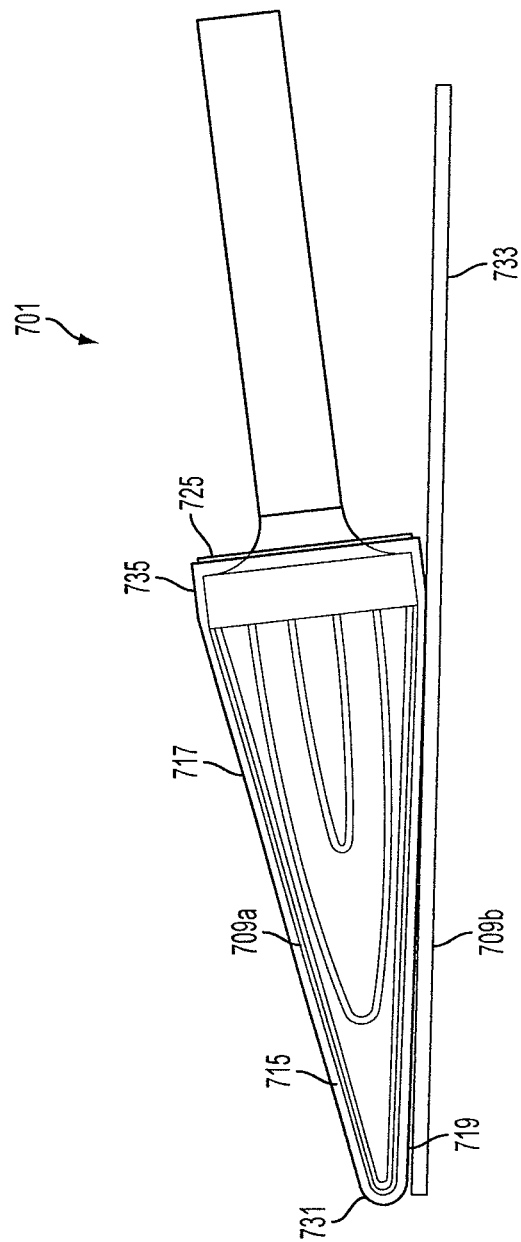
FIGS. 18 and 19 are side views of the steam frame of FIG. 15, with a steam towel attached.
Figure 19:
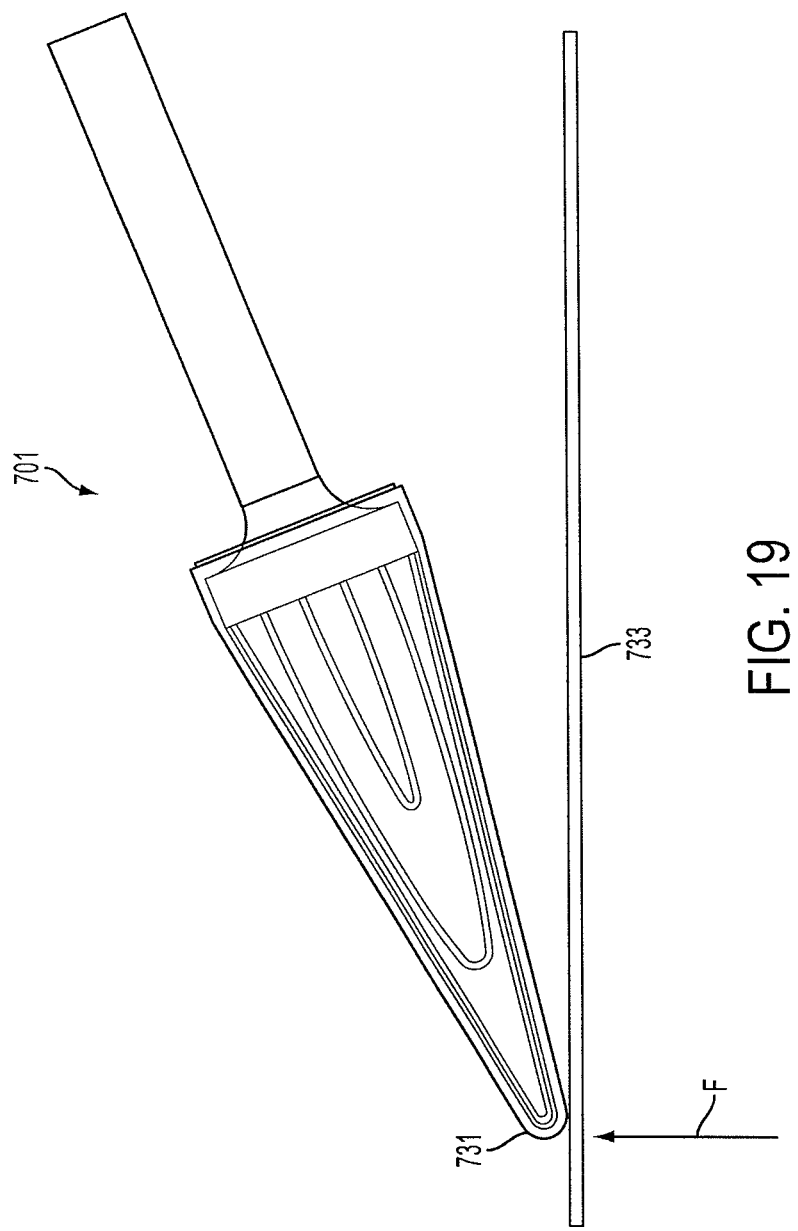

In use and as shown in FIGS. 17 and 18, a towel 715 or cloth or the like in the form of a steam pocket may be positioned or slipped over wires 709 and base 703. As best seen in FIGS. 18 and 19, the pocket may have a substantially triangularly-shaped cross-sectional profile, with the towel 715 having an upper surface 717, a lower surface 719, two side surfaces 721, 723, and a back surface 725, the back surface 725 having at least one opening or split. The towel 715 may be positioned over the wires 709 and at least a portion of the base 703, with the towel 715 being releasably secured or positioned about the wires 709 and base 703 by closing or securing the at least one opening or split of the back surface 725 with Velcro strips or plastic zippers or the like. After releasably securing the towel over the wires 709 and the base 703, upper surface 717, lower surface 719, side surfaces 721, 723 and base 703 are spaced apart to create a space 727 therebetween (e.g., where steam is introduced). In an exemplary embodiment, space 727 has a substantially triangularly-shaped cross-sectional profile. Base 703 typically includes a steam outlet 707 for the introduction and distribution of steam to the space 727. In exemplary embodiments, the steam outlet is trumpet-shaped or bell-shaped to ensure even steam distribution throughout space 727. In general, the towel 715 overlaps the base 703 to seal openings that may leak steam. Thus, the steam exits the space 727 of the pocket by penetrating the fabric of the towel 715.

In general, the upper set of wires 709a, lower set of wires 709b, and two side sets of wires 709c, 709d are configured and dimensioned to flex and/or bend to take the shape of the towel 715. For example, when the towel 715 is removed from the wires 709, the wires 709 may be substantially straight (e.g., the wires 709 may be substantially straight and substantially perpendicular to a plane of the base 703, as shown in FIGS. 15-16). However, when the towel 715 is placed over the wires 709, the elasticity of the wires 709 allows them to bend and/or flex to take the shape of the towel 715, thereby forming space 727 (e.g., space 727 having the substantially triangularly-shaped cross-sectional profile, as shown in FIGS. 17-18). With the towel 715 positioned over the wires 709, the wires 709 are bent and under tension. In exemplary embodiments, this tension ensures that the towel 715 remains stretched, taut and/or tight on the frame 701. The elasticity of the wires 709 thus allows for greater tolerances in the production of towel 715 (e.g., the wires 709 allow various sized towels 715 to be placed over them under tension), thereby providing a significant commercial and manufacturing advantage as a result. In addition, in exemplary embodiments, the design of frame 701 allows for the independent bending and/or flexing of each wire 709. This allows the towel 715 positioned over the wires 709 to wrap around various surfaces (e.g., uneven surfaces) to be cleaned, thereby adding more versatility to the frame 701, and thus providing another significant commercial and manufacturing advantage as a result.

Moreover, when the frame 701 with the towel 715 positioned over the wires 709 is pressed against a surface to be cleaned (e.g., a substantially flat surface), the frame 701 remains relatively stiff, which improves the scrubbing action of the towel 715 on the cleaning surface. In exemplary embodiments, when the frame 701 with the towel 715 positioned over the wires 709 is pressed against a surface to be cleaned, forces inside the towel 715 and/or wires 709 immobilize the wires 709, and creates a link between at least an upper wire 709*a* and a lower wire 709*b*, thereby increasing support for the towel 715. For example and as shown in FIG. 19, the shape of the towel 715 at the distal tip 731 ensures that at least an upper wire 709*a* and a lower wire 709*b* remain interlocked when a force F is applied to the frame 701 (e.g., when the frame 701 is pressed against a surface 733 to be cleaned). This interlocking or linkage greatly increases the rigidity of frame 701 and increases the force necessary to bend the frame 701. In an exemplary embodiment and as shown in FIG. 19, the upper wires 709*a* may have a higher angle toward the cleaning surface 733, thereby allowing the upper wires 709*a* to provide greater support against bending. In addition, the lower wires 709*b* may have a lower angle toward the cleaning surface 733, thereby allowing the lower wires 709*b* to bend easier, thereby ensuring that at least an upper wire 709*a* and a lower wire 709*b* remain interlocked when a force F is applied to the frame 701 (e.g., when a cleaning surface 733 upward reactive force F is applied to the frame 701).

In an exemplary embodiment and as shown in FIG. 17, once the towel 715 has been placed over the wires 709 to form the space 727 (e.g., space 727 having the substantially triangularly-shaped cross-sectional profile), the substantially flat lower surface 719 of the towel 715 may be positioned on or above and substantially parallel to a surface 733 to be cleaned. Such positioning of the frame 701 allows the handle 702 to be positioned at a higher position from the cleaning surface 733, thereby allowing more space for a user's hand between the handle 702 and the cleaning surface 733. This positioning feature of the frame 701 substantially eliminates the need for extra connections for the frame 701 (e.g., extra handle 702 connections for the user), and simplifies the production and/or design of the frame, thereby providing a significant commercial and manufacturing advantage as a result. Moreover, the fixedly attached or coupled connection between the handle 702 and the base 703 improves a user's control of the frame 701 during use. As shown in FIG. 18, the low profile distal or front edge or portion 731 of the frame 701 allows for the cleaning of narrow spaces or small surfaces or crevices or the like, and the higher profile proximal portion or region 735 of the frame 701 allows for the efficient cleaning of corner surfaces or the like (e.g., allows for the cleaning of corner surfaces or the like in one pass).

By providing a steam frame with flexible wires or bands that form a skeleton or flexible frame with a steam towel to form an internal space for distribution of steam, the device has the needed flexibility for cleaning various surfaces (e.g., uneven surfaces and tight corner areas). The added flexibility of attaching to a steam hose of a steam appliance or directly to the steam outlet of a hand steamer provides added utility.

For purposes herein, the terms "connect", "connected", "connection", "attach", "attached" and "attachment" refer to direct connections and attachments, indirect connections and attachments, and operative connections and attachments. For example, steam applicator 102 is considered to be connected to steam conduit 110 even though steam applicator is directly connected to handle 107 which is, in turn, connected to steam conduit 110. Also for purposes herein, the terms "connectable", "attachable", "removable", etc. refer both to components which can be connected, attached, removed, etc., and also refer to components which are connected, attached and removed.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A steam applicator frame for supporting a steam-permeable material, comprising:
 a base having a single plane;
 at least four support elements, wherein each of the four support elements contacts the base and extends laterally from the base and arranged such that the base and the four support elements define an elongated chamber, wherein the spacing between the first support element and the second support element defines a first gap and the spacing between the third support element and the fourth support element defines a second gap, each of the first gap and second gap operable to permit the passage of steam therethrough, and wherein the first gap and the second gap are substantially transparent as viewed from the first gap through and to the second gap; and
 a steam inlet opening within the single plane to introduce steam into the chamber, the single plane extends perpendicular to the steam inlet opening, wherein:
 a distal end of the chamber is open and substantially free of the four support elements.

2. A steam applicator frame as in claim 1, in combination with:
 a steam-permeable material constructed and arranged to be placed over the steam applicator frame; and
 a handle attachable to a proximal end of the steam applicator frame.

3. A combination as in claim 2, wherein the steam-permeable material and the steam applicator frame form a wedge shaped steam applicator.

4. A combination as in claim 2, further comprising:
 a steam generation unit; and
 a steam conduit attached to the steam generation unit and the steam applicator frame.

5. A combination as in claim 3, wherein the steam conduit comprises a flexible hose.

6. A steam applicator frame as in claim 1, wherein a flexibility of the frame increases toward a distal end of the frame.

7. A steam applicator as in claim 6, further comprising tapering support ribs on the four support elements.

8. A steam applicator frame as in claim 1, wherein the chamber has an elongated cylindrical shape.

9. A steam applicator frame as in claim 8, further comprising a steam-permeable shaggy material positioned over the four support elements.

10. A steam applicator frame as in claim 1, wherein the four support elements have a tapering diameter.

11. A steam applicator frame for supporting a steam-permeable material, comprising:
 a base having a single plane;
 at least four support elements, wherein each of the four support elements contacts the base and extends laterally from the base and arranged such that the base and the four support elements form an elongated chamber, wherein the distal end of the chamber is open and free of the four support elements; and a steam inlet opening within the single plane to introduce steam into the steam applicator frame, the single plane extends perpendicular to the steam inlet opening, wherein exterior surfaces of the four support elements are substantially planar and the first support element is substantially co-planar with the second support element and the third support element is substantially co-planar with the fourth support element, wherein a first gap is formed between the first support element and the second support element and a second gap is formed between the third support element and the fourth support element, the first and second gaps operable to permit the passage of steam therethrough, and wherein the first gap and the second gap are substantially transparent as viewed from the first gap through and to the second gap.

12. A steam applicator frame as in claim 11, in combination with:

a steam-permeable material constructed and arranged to be placed over the steam applicator frame; and a handle attachable to the steam applicator frame.

13. A combination as in claim 12, further comprising:

a steam generation unit; and a steam conduit attached to the steam generation unit and the steam applicator frame.

14. A combination as in claim 13, wherein the steam applicator frame has an elongated cylindrical shape.

15. A steam applicator frame for supporting a steam-permeable material, comprising:

a base having a single plane;

a handle extending from the base;

at least four support elements, wherein each of the four support elements contacts the base and extends laterally from the base and arranged such that a steam-permeable material is capable of being placed over the four support elements to form steam-permeable surfaces, wherein the first support element and the second support element are configured to define a first gap and the third support element and the fourth support element are configured to define a second gap, the first and second gaps operable to permit the passage of steam therethrough, and wherein the first gap and the second gap are substantially transparent as viewed from the first gap through and to the second gap;

a steam inlet opening within the single plane to introduce steam into the steam applicator frame, the single plane extends perpendicular to the steam inlet opening; and a steam-impermeable barrier positioned between the handle and the four support elements, wherein the distal portion of the steam applicator frame is substantially free of the four support elements so as to permit the steam to pass therethrough to the steam-impermeable barrier.

16. A steam applicator frame as in claim 15, wherein the base comprises the steam-impermeable barrier.

17. A steam applicator frame as in claim 15, in combination with:

a steam-permeable material constructed and arranged to be placed over the steam applicator frame.

18. A steam applicator comprising:

a steam-permeable material in the shape of a bag;

a frame supporting the steam-permeable material, the frame including:

a base having a single plane;

at least four support elements, wherein each of the four support elements contacts the base and extends laterally from the base, the steam-permeable material configured to be positioned over the four support elements, wherein the spacing between the first support member and the second support member defines a first gap and the spacing between the third support member and the fourth support member defines a second gap, and wherein the first gap and the second gap are substantially transparent as viewed from the first gap through and to the second gap; and a steam inlet opening within the single plane to introduce steam into an interior volume of the frame, the single plane extends perpendicular to the steam inlet opening, wherein the four support elements are arranged such that when steam is introduced into the interior volume, the steam can flow through the first gap and the second gap, and at least a first surface of the steam-permeable material and a second surface of the steam-permeable material, each of the first and second surfaces extending directly from the base, and the first surface converges with the second surface to form an angle, wherein the angle is substantially free of the support elements so as to allow the steam to flow evenly throughout the bag.

19. A steam applicator frame as in claim 18, wherein the first surface converges with the second surface to form a right angle.

20. A steam applicator as in claim 18, in combination with:

a steam generation unit; and a steam conduit attached to the steam generation unit and the steam applicator.

21. A steam applicator frame for supporting a steam-permeable material, comprising:

a base having a single plane;

at least three support elements, wherein each of the three support elements contacts the base and extends laterally from the base and arranged such that the base and the three support elements form an elongated chamber;

a steam inlet opening within the single plane to introduce steam into the steam applicator frame, the single plane extends perpendicular to the steam inlet opening, wherein the three support elements are arranged to form three gaps in three surfaces of the chamber, wherein the first support element and the second support element form a first gap defining a first surface, the second support element and the third support element form a second gap defining a second surface, and the third support element and the first support element form a third gap defining a third surface, wherein the first gap and the second gap are substantially transparent as viewed from the first surface to the second surface, wherein the second gap and the third gap are substantially transparent as viewed from the second surface to the third surface, wherein the third gap and the first gap are substantially transparent as viewed from the third surface to the first surface, and wherein each of the three surfaces extending directly from the base, and wherein each of the three surfaces is on its own plane.

22. A steam applicator frame as in claim 21, in combination with steam-permeable material and handle which is attached to the frame.

23. A combination as in claim 22, further comprising a steam generation unit and a steam conduit which is attached to the steam generation unit and the steam applicator frame.

24. A steam applicator frame for supporting a steam-permeable material, comprising:
a base having a single plane;
at least four support elements, wherein each of the four support elements contacts the base and extends laterally from the base substantially parallel or angled towards each other and arranged such that a steam-permeable material is configured to be placed over the four support elements;
a steam inlet opening within the single plane to introduce steam into the steam applicator frame, the single plane extends perpendicular to the steam inlet opening,
wherein a first surface is formed between the first support member and the second support member, a second surface is formed between the second support member and the third support member, a third surface is formed between the third support member and the fourth support member, and a fourth surface is formed between the fourth support member and the first support member, wherein the first surface and the third surface are substantially transparent as viewed from the first surface to the third surface, wherein the second surface and the fourth surface are substantially transparent as viewed from the second surface to the fourth surface,
wherein the four support elements are arranged such that when a steam-permeable material is placed over the four support elements, and steam is introduced into the steam applicator frame, the steam can flow through the four surfaces of the steam-permeable material, and
wherein each of the four surfaces of the steam-permeable material is on a separate plane extending from the base.

25. A steam applicator frame as in claim 24, in combination with:
the steam-permeable material to form a steam applicator;
a steam generation unit; and
a steam conduit to guide steam from the steam generation unit to the steam applicator frame.

* * * * *